(12) United States Patent
Gallup et al.

(10) Patent No.: US 7,839,969 B2
(45) Date of Patent: Nov. 23, 2010

(54) DEVICE AND METHOD FOR DETECTING DEPOSITION ON AN INNER SURFACE OF A PIPE

(75) Inventors: Darrell Lynn Gallup, Houston, TX (US); Christopher Henry Spurrell, Hawthorne, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 21 days.

(21) Appl. No.: 12/109,194

(22) Filed: Apr. 24, 2008

(65) Prior Publication Data

US 2009/0268868 A1    Oct. 29, 2009

(51) Int. Cl.
*G01N 23/223* (2006.01)
*H05G 1/02* (2006.01)

(52) U.S. Cl. .............................. 378/45; 378/44; 378/198
(58) Field of Classification Search ................. 378/44, 378/45, 46, 47, 49, 50, 59, 60, 198
See application file for complete search history.

(56) References Cited

U.S. PATENT DOCUMENTS

| | | | | |
|---|---|---|---|---|
| 3,937,953 | A * | 2/1976 | Stafford et al. | 378/44 |
| 4,146,791 | A * | 3/1979 | Dahl et al. | 378/59 |
| 4,244,296 | A * | 1/1981 | Vertut | 104/138.2 |
| 4,435,829 | A | 3/1984 | Siler et al. | |
| 4,510,573 | A * | 4/1985 | Boyce et al. | 702/23 |
| 4,862,808 | A * | 9/1989 | Hedgcoxe et al. | 104/138.2 |
| 5,142,989 | A * | 9/1992 | Suzumori et al. | 104/138.2 |
| 5,369,578 | A * | 11/1994 | Roscoe et al. | 702/8 |
| 5,371,363 | A * | 12/1994 | Lilimpakis | 250/253 |
| 5,437,772 | A | 8/1995 | De Castro et al. | |
| 5,565,633 | A | 10/1996 | Wernicke | |
| 6,097,785 | A * | 8/2000 | Elam | 378/45 |
| 6,350,372 | B1 * | 2/2002 | Degnan et al. | 208/251 R |

(Continued)

FOREIGN PATENT DOCUMENTS

JP    06-213837 A    8/1994

(Continued)

OTHER PUBLICATIONS

Gallup, D.L., External Surveillance of Geothermal Scale Deposits Employing Iridium-192 Radiography, Geothermal Resources Counsel, vol. 10, pp. 317-322 (Sep. 1986).

(Continued)

*Primary Examiner*—Allen C. Ho (57) ABSTRACT

A method and device for detecting mercury or other material deposits on an inner surface of an enclosed passage are provided. The device includes a detection unit that is adapted to be transported through the passage, and the detection unit includes a radiation source and an x-ray fluorescence detector. The radiation source is configured to emit a radiation emission toward the inner surface of the passage to excite a portion of the inner surface, and the x-ray fluorescence detector is configured to detect a resulting x-ray emission from the portion of the inner surface to identify a material deposit on the inner surface. The detection unit can identify material deposits at successive positions along a length of the passage and thereby generate a plurality of data points, each data point providing an indication of a material deposit existence for a corresponding position along the length of the passage.

23 Claims, 4 Drawing Sheets

U.S. PATENT DOCUMENTS

| | | | | |
|---|---|---|---|---|
| 6,754,304 | B1 * | 6/2004 | Kumakhov | 378/45 |
| 7,192,188 | B2 * | 3/2007 | Maschke | 378/197 |
| 7,564,948 | B2 * | 7/2009 | Wraight et al. | 378/101 |
| 2007/0246649 | A1 * | 10/2007 | Jacobi et al. | 250/269.6 |

FOREIGN PATENT DOCUMENTS

| | | |
|---|---|---|
| JP | 07-159145 A | 6/1995 |
| JP | 07-333176 A | 12/1995 |

OTHER PUBLICATIONS

Sarrazin, P., et al., Processes Prevent Detrimental Effects from As and Hg in Feedstocks, Oil & Gas Journal, Jan. 25, 1993, pp. 86-90, available from http://www.osti.gov/energycitations/product.biblio.jsp?osti_id=7052928.

Pasmore, James R., et al., Portable Tools Pack Plenty of Analyzing Power, Inspection Trends, vol. 8, No. 1, Jan. 2005, available from: http://www.niton.com/Documents/alloy/Inspection_Trends_012005_web.pdf.

Thermo Fisher Scientific Inc., "Thermo Scientific, Metal & Alloy Analysis" printed Feb. 15, 2008, pp. 1-2, available at http://www.niton.com/Metal-and-Alloy-Analysis/default.aspx.

Thermo Fisher Scientific Inc., "Quality Control of Metal Alloys in the Manufacturing and Metal Fabrication Industries, Thermo Scientific NITON XL3 Series Handheld Alloy Analyzers-Simply Superior XRF", Jul. 2007, pp. 1-4, available at http://www.niton.com/Documents/alloy/8-303_0907_Fab_App_bull_low_web.pdf.

Thermo Fisher Scientific Inc., "Positive Material Identification and Analysis of Metals and Alloys in the Petrochemical Industries, Thermo Scientific NITON XL3 Portable Alloy Analyzers-Simply Superior XRF", Jul. 2007, pp. 1-4, available at http://www.niton.com/Documents/alloy/18-302_0907_PMI_App_bull_low_web.pdf.

Thermo Electron Corporation, "Use of Portable XRF in the FAC Inspection Protocol", 2005, pp. 1-2, available at http://www.niton.com/Documents/alloy/Old%20Gen%20Apps/8-304_0805_FAC_AppBulletin_web.pdf.

Thermo Fisher Scientific Inc., "Sorting, Identification and Analysis of Metals and Alloys in the Recycling Industry, Thermo Scientific NITON XL3 Handheld Alloy Analyzers-Simply Superior", Jul. 2007, pp. 1-4, available at http://www.niton.com/Documents/alloy/8-301_0907_Scrap_App_bulletin-lowres_web.pdf.

Thermo Fisher Scientific Inc., "Thermo Scientific NITON XL3t", Product Specifications, 2007, pp. 1-2, available at http://www.niton.com/Documents/XL3-spec-sheets/T-201_0407_XL3t_spec_sheet_web.pdf.

Thermo Fisher Scientific Inc., "Thermo Scientific NITON XL3p", Product Specifications, 2007, pp. 1-2, available at http://www.niton.com/Documents/XL3-spec-sheets/P-201_0407_XL3p_spec_sheet_web.pdf.

Thermo Fisher Scientific Inc., "Thermo Scientific NITON XLt/XLp/Xli 800, The World Standard in Portable Alloy Analysis", 2007, pp. 1-2, available at http://www.niton.com/Documents/Old-gen-Spec-Sheets/8-214_0107_XLt-p-i_800_Spec_Sheet_web.pdf.

Thermo Fisher Scientific, "Thermo Scientific NITON XLt 898He", 2007, pp. 1-2, available at http://www.niton.com/Documents/spec-sheets/8-215_0807_XLt_898He_Spec_Sheet_web.pdf.

Thermo Fisher Scientific, Inc., "Thermo Scientific, Toys and Lead are a hazardous combination", printed Feb. 15, 2008, pp. 1-2, available at http://www.niton.com/NITON-Analyzers-Products/default.aspx.

Thermo Fisher Scientific, Inc., "Thermo Scientific, NITON XRF analyzers, Positive Material Identification (PMI)", printed Feb. 15, 2008, pp. 1-2, available at http://www.niton.com/Metal-and-Alloy-Analysis/Applications/pmi.aspx.

Thermo Fisher Scientific, Making Contact with Positive Material Identification, Oct. 2007, pp. 1-2, available at http://www.niton.com/Documents/alloy/NDT_PMI_Article_10_2007_web.pdf.

PCT International Search Report dated Jan. 5, 2010 for PCT Application No. PCT/US2009/036610.

* cited by examiner

DEVICE AND METHOD FOR DETECTING DEPOSITION ON AN INNER SURFACE OF A PIPE

BACKGROUND OF THE INVENTION

1. Field of the Invention

This invention relates to the detection of materials deposited on the inner surface of a passage and, more particularly, a device and method for detecting mercury or other material deposits in a passage, such as a pipe through which hydrocarbon fluids are delivered.

2. Description of Related Art

Hydrocarbon fluids, such as crude oil, are often delivered through carbon steel pipes and other passages during and between operations for production, processing, storing, and the like. Some hydrocarbon fluids include mercury or other metals, which can be deposited onto the inner surface of the pipes as the hydrocarbon fluid passes therethrough. In some cases, a thin film of mercury or other materials can build up on the inner surface of the pipe. Such deposited mercury or other materials can present an environmental hazard and can be absorbed back into hydrocarbons passing through the pipe, such that even if a hydrocarbon fluid does not contain significant amounts of the mercury or other deposited material, the fluid can be contaminated by the mercury or other deposited material in the pipe.

When a pipe or other tubular passage becomes contaminated with mercury or other materials on its inner surface, a decontamination or cleaning operation is typically performed to remove the mercury or other materials. For example, the pipe can be drained of the hydrocarbon fluid and a cleaning fluid and/or a cleaning device can be passed through the pipe to remove the deposited mercury or other materials. Such cleaning operations can be performed at regular intervals or only when required. For example, mercury in the pipe can be detected in order to determine whether such a cleaning operation must be performed.

One conventional method for detecting mercury inside a pipe uses a strong source of x-ray radiation that can penetrate the pipe. The source of x-ray radiation is positioned near the pipe and directed toward the pipe so that the radiation passes through the pipe and impinges on a detection material, or x-ray film, on the opposite side of the pipe. The exposure of the detection material to the radiation is determined according to the type of the pipe as well as any mercury or other materials that are deposited inside the pipe. Thus, by examining the exposed detection material and identifying contrasting light and dark portions of the detection material, an operator can determine whether some portions of the pipe have internal deposits. For example, if liquid mercury has been deposited on a small spot on the inner surface of the pipe, the mercury will decrease the passage of x-rays so that the corresponding portion of the detection material (x-ray film) is less developed and is lighter than the surrounding areas. Thus, if the detection material includes a small, light spot that is lighter than the surrounding portions, the operator might conclude that the light spot represents an area of the pipe where the inner surface has a deposit of liquid mercury or other material. Similarly, mercury oxide and sulfide deposited on the inner surface of the pipe show up on the x-ray film as dark and white combinations that are different in contrast on the film than the pipe material.

While such an x-ray detection method has been used to determine local deposits of mercury and other materials, deposits can sometimes be difficult to detect using this conventional method. For example, if the pipe has a uniform film of mercury deposited on its inner surface, the operator may not detect any contrast between the different portions of the detection material and therefore may be unable to identify any deposit. Also, if other materials are deposited in the pipe, the other materials can also block the x-rays, such that the operator may be unable to determine what type of deposits have formed in the pipe. In addition, this conventional method typically requires safeguards to be taken to contain the strong x-ray radiation that is generated so that the radiation is not spread to equipment and/or people in the area.

Thus, a need exists for an improved method and device for detecting mercury and/or other materials that have been deposited on the inner surface of a pipe or other passage. The method should be capable of detecting deposits that are uniform over the inner surface, e.g., if the entire inside surface is coated with a film of material. Preferably, the method should be adapted to operate without the use of a strong x-ray machine and x-ray film.

SUMMARY OF THE INVENTION

The embodiments of the present invention generally provide a method and device for detecting material deposits on an inner surface of an enclosed passage, such as a pipe, using x-ray fluorescence (XRF) that is emitted from the inner surface. The method does not require contrast between different portions of the inner surface and therefore can detect deposits even if the entire inner surface is coated with a film of material. In addition, the inner surface can be excited by radiation emitted within the passage, and the XRF emission from the inner surface can be detected within the passage, such that the method is capable of being performed without requiring strong x-ray emissions that can penetrate the walls of the passage.

According to one embodiment of the present invention, the method includes transporting through the passage a detection device that includes an x-ray fluorescence detection unit. The x-ray fluorescence detection unit is operated so that the detection unit in the passage emits a radiation emission toward the inner surface of the passage to excite a portion of the inner surface and detects a resulting x-ray emission from the portion of the inner surface to identify a deposit of mercury or other material on the inner surface. The step of operating the XRF detection unit is repeated with the detection unit at successive positions along a length of the passage to thereby generate a plurality of data points, each data point providing an indication of a deposit existence for a corresponding position along the length of the passage. The detection device can also be used to identify other materials, e.g., any of a plurality of materials at the inner surface of the passage.

In some cases, the method includes providing a line that is connected to the detection device, and the detection device is pulled through the passage via the line extending through the passage. A plurality of wheels can be provided for supporting the detection unit in the passage, and at least one of the wheels can be driven to thereby advance the detection unit through the passage.

The method can include storing information that is representative of the data points in a memory of the detection device and subsequently outputting the information from the detection device, e.g., to a computer or other receiver outside of the passage. In some cases, information representative of the data points can be communicated from the detection device while the detection device is disposed in the passage, e.g., by communicating the information wirelessly to a receiver disposed outside of the passage or via a wire extending from the detection device to a receiver disposed outside of the passage.

According to one aspect of the present invention, the operation of the detection unit includes rotating a detection head of the detection unit to thereby detect emissions from a plurality of portions defining an arc on the inner surface of the passage. In addition or alternative, a plurality of detectors can be operated to thereby detect emissions from a plurality of portions defining an arc on the inner surface of the passage.

In some cases, the detection device can be transported through the passage while the passage is at least partially full of liquid hydrocarbon, and the detection unit can be operated to emit the radiation emission through the liquid hydrocarbon to the inner surface of the passage and detect the resulting x-ray emission from the inner surface through the liquid hydrocarbon. The detection unit can be positioned proximate the inner surface, e.g., within 1 inch of the inner surface of the passage.

A detection device according to another embodiment of the present invention includes a detection unit that is adapted to be transported through the passage. The detection unit includes a radiation source that is configured to emit a radiation emission toward the inner surface of the passage to excite a portion of the inner surface and an x-ray fluorescence detector that is configured to detect a resulting x-ray emission from the portion of the inner surface to identify a deposit on the inner surface. The detection unit is configured to identify deposits at successive positions along a length of the passage and thereby generate a plurality of data points. Each data point provides an indication of a deposit existence for a corresponding position along the length of the passage. The detection unit can be configured to identify mercury, other metals, or other materials, e.g., any of a plurality of materials at the inner surface of the passage.

In some cases, the detection device include an elongate flexible line that is connected to the detection device, e.g., so that the line can extend from the passage while the detection device is disposed in the passage and the line can be used to pull the device through the passage. A plurality of wheels can be connected to the detection unit and configured to support the detection unit in the passage, and a drive device can optionally be provided and configured to rotate at least one of the wheels to thereby advance the detection unit through the passage.

The detection device can include an electronic memory that is in communication with the detection unit, and the memory can be adapted to store information representative of the data points and subsequently output the information from the detection device. In addition, or alternative, a communication device in the detection device can be in communication with the detection unit and configured to communicate information representative of the data points from the detection device while the detection device is disposed in the passage, e.g., to a receiver disposed outside of the passage. The communication device can be configured to communicate the information wirelessly to a receiver disposed outside of the passage and/or via a wire extending from the detection device to a receiver disposed outside of the passage.

According to one aspect of the present invention, the detection device defines a rotatable head. The head defines the detector so that the detector is configured to be rotated within the passage and thereby detect emissions from a plurality of portions defining an arc on the inner surface of the passage. In addition or alternative, the detection device can include a plurality of detectors that are configured to detect emissions from a plurality of portions defining an arc on the inner surface of the passage.

In some cases, the detection device can be configured to operate in the passage while the passage is at least partially full of liquid hydrocarbon, and the detection unit can be configured to emit the radiation emission through the liquid hydrocarbon to the inner surface of the passage and detect the resulting x-ray emission from the portion of the inner surface through the liquid hydrocarbon. The detection unit can be configured to be positioned proximate the inner surface, e.g., within 1 inch of the inner surface of the passage, when the detection device is transported through the passage.

BRIEF DESCRIPTION OF THE DRAWINGS

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

Figure 1:
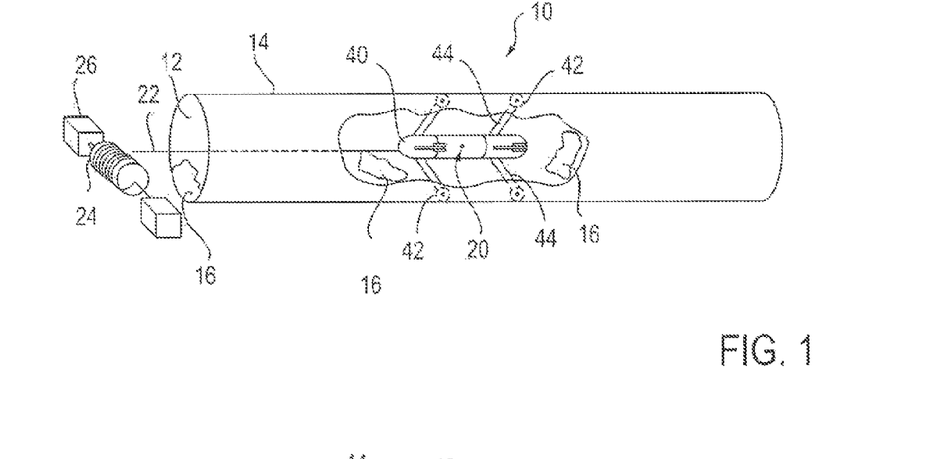
FIG. 1 is a partial cut-away view illustrating a device for detecting material deposits on an inner surface of a passage according to one embodiment of the present invention.

Referring now to the drawings and, in particular, to FIG. 1, there is shown a detection device 10 for detecting a material such as mercury that has been deposited on the inner surface 12 of a pipe or other enclosed passage 14. In particular, the detection device 10 can be used to detect deposits 16 that have been formed on the inside of the passage 14 from hydrocarbon fluids that are delivered through the passage 14, e.g., pipes used in an upstream or downstream process, such as for transporting crude oil, natural gas, refined hydrocarbon products, and/or other hydrocarbon fluids between wells, storage facilities, refineries or other processing facilities, and the like. The deposits 16 can be formed of mercury and/or other materials. The detection device 10 can be used to determine whether the passage 14 needs to be cleaned to remove the deposits 16 and/or whether (and to what extent) a cleaning operation has successfully removed the deposits 16 from the passage 14.

Figure 3:
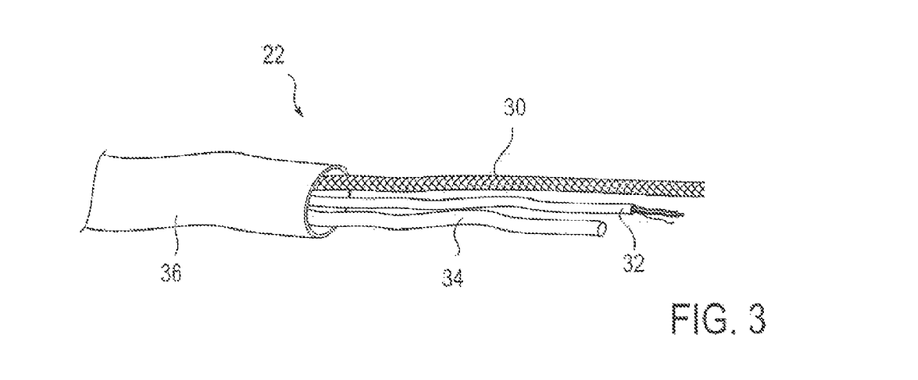
FIG. 3 is a perspective view illustrating a portion of the flexible line of FIG. 1.

The detection device 10 generally includes a detection unit 20 that is adapted to be transported through the passage 14 to detect one or more materials on the inner surface 12 of the passage 14. As shown in FIG. 1, a flexible line 22 such as a cable, rope, chain, or the like can extend from the detection device 10, and the flexible line 22 can be used to transport the detection device 10 through the passage 14. For example, one end of the line 22 can be connected to the detection device 10 and the opposite end of the line 22 can be wound onto a roller or spool 24 or other take-up apparatus, which can be rotated by a motor 26. As the motor 26 rotates the spool 24, the detection device 10 is pulled by the line 22 toward the spool 24. As shown in FIG. 3, the flexible line 22 can include a strong tensile-bearing component 30, such as a cable of twisted metal strands, a rope, or a chain. In addition, the line 22 can include an electrical wire 32 and/or a hydraulic or pneumatic tubular hose 34 for communication of information and/or power. The component 30, wire 32, and the hose 34 can be disposed in a common sheath 36. It is appreciated that the line 22 can also include fiber optic cables or other communication media.

The detection device 10 can be transported through a passage 14 that is disposed horizontally, as shown in FIG. 1, or through passages that are oriented vertically or at any angle. In some cases, the detection device 10 can move downward through the passage 14, so that the weight of the detection device 10 facilitates the movement thereof, and/or the line 22 can be used to slow or otherwise control the movement of the detection device 10 through the passage 14. The detection device 10 can also be used in passages other than pipes, such as storage containers, processing facilities, and the like.

Figure 2:
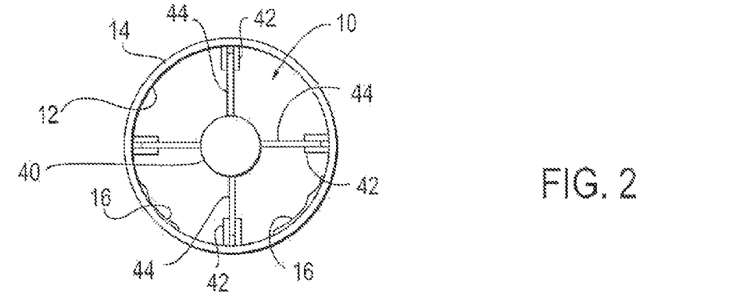
FIG. 2 is an elevation view illustrating the device of FIG. 1, as seen from one end of the passage.

The detection device 10 defines a housing 40 and can include one or more contact members that extend from the housing 40 for making rolling, sliding, or other contact with the inner surface 12 of the passage 14. In particular, as shown in FIGS. 1 and 2, the detection device 10 includes contact members that are wheels 42 that extend from the housing 40 of the detection device 10. The wheels 42 can be supported by arms 44 that connect to the housing 40. More particularly, the arms 44 can be hingedly connected to the housing 40 and biased by springs to push the wheels 42 outward against the inner surface 12. In this way, the wheels 42 can maintain contact with the inner surface 12, even when the detection device 10 is transported through passages 14 of different sizes and/or the detection device 10 is transported through bends, tapers, and other nonuniform portions of the passage 14. The wheels 42 can be rotatably connected to the arms 44 so that the wheels 42 make rolling contact with the inner surface 12 of the passage 14 as the detection device 10 is transported therethrough. Alternatively, the detection device 10 can define other contact surfaces that slide along the inner surface 12. In either case, the detection device 10 can be configured so that the detection unit 20 is transported either along a central axis of the passage 14, as shown in FIG. 2, or closer to one side of the passage 14.

Figure 4:
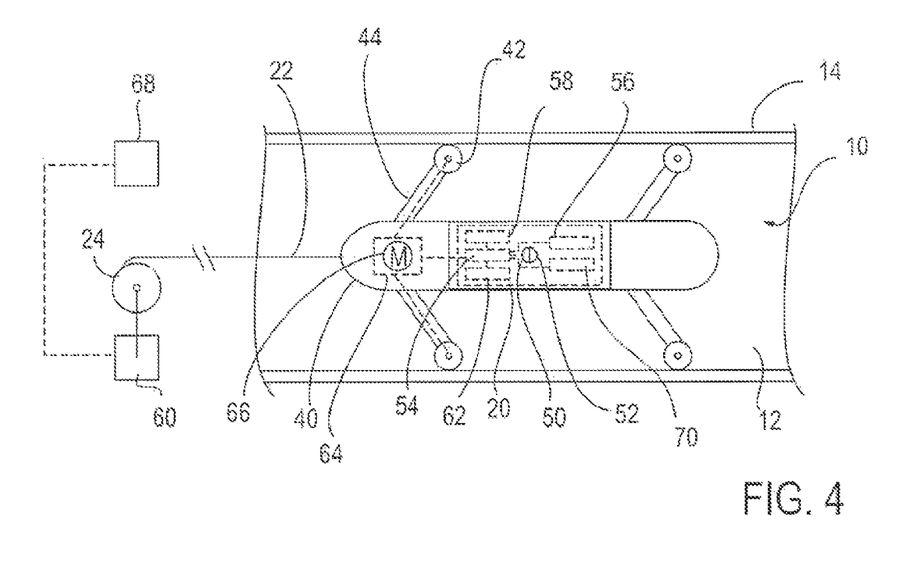
FIG. 4 is an elevation view illustrating the device of FIG. 1, as seen within the passage.

As shown in FIG. 4, the detection unit 20 includes a radiation source 50 and an x-ray fluorescence (XRF) detector 52. The radiation source 50 is configured to emit a radiation emission, such as an emission of x-rays or gamma rays, toward a portion of the inner surface 12 of the passage 14, and the x-ray fluorescence detector 52 is configured to detect an x-ray emission that results from the excited portion of the inner surface 12. The radiation source 50 and the XRF detector 52 can be an integral device, as shown in FIG. 4, or can be two separate devices.

X-ray fluorescence refers to the emission from a material that has been excited, e.g., by x-rays or gamma rays, of x-rays that are characteristic of the elemental content of the material. As is conventionally known, XRF can be used to identify a material according to the characteristic or fluorescent x-rays that are emitted by the excited material. For example, the fluorescent radiation that is emitted can be analyzed according to either the energies of the photons that are emitted ("energy-dispersive analysis") or the wavelengths of the radiation that is emitted ("wavelength-dispersive analysis"). Using such conventional XRF techniques, particular materials can be distinguished from other materials. For example, mercury, arsenic, selenium, silt/dirt, unstable salts such as calcium napthenates can be distinguished from the iron in carbon steel or the nickel, chromium, and other elements in other metal materials of the pipeline.

The radiation source 50 and the XRF detector 52 communicate with a controller 54 that controls the operation of the radiation source 50 and the detector 52. The controller 54 can operate the source 50 and/or detector 52 continuously or intermittently, e.g., to emit and/or detect pulses of radiation. In either case, the radiation source 50 emits radiation toward the inner surface 12 of the passage 14 so that the radiation excites the material of the inner surface 12. If the passage 14 is free of deposits 16, the surface 12 will be defined by the material of the passage 14, e.g., steel, iron, polymer liners, or the like. If deposits 16 have formed on the inside of the passage 14, the inner surface 12 will be defined by the material of the deposits 16. Thus, if mercury or another material of interest has been deposited on the inner surface 12 at the position that is being identified, the mercury or other material will be excited by the radiation emitted by the source 50 and, in turn, emit a characteristic radiation that is detected by the detector 52 and by which the detector 52 can determine that the inner surface 12 is defined by the mercury or other material deposit 16.

The detection unit 20 can operate continuously or intermittently as the detection device 10 is transported through the passage 14 to perform a plurality of detection operations at successive positions along the length of the passage 14. In this way, the detection device 10 can determine whether mercury or another material has been deposited at the inner surface 12 of the passage 14 at a plurality of successive positions corresponding to successive portions of the inner surface 12 along the length of the passage 14. The detection device 10 typically generates a data point at each position, i.e., for each portion of the surface 12 that is identified, and each data point provides an indication of a deposit 16 existence for a corresponding portion at a corresponding position along the length of the passage 14. For example, the detection unit 20 can move at a predetermined speed through the passage 14, and the detection unit 20 can perform individual detection operations at predetermined time intervals, so that a data point is generated for a plurality of positions at known intervals along the length of the passage 14. In some cases, the detection unit 20 can sense or otherwise determine its own position in the passage 14, e.g., using a position sensor 56, such as a global positioning device, a measuring wheel that measures the movement of the detection unit 20 through the passage 14, or the like. Each data point generated by each successive detection operation can include information such as a location in the passage 14 (longitudinal and/or radial location) and one or more wavelength and/or intensity of radiation received by the XRF detector 52 at the corresponding location. In some cases, the controller 54 can be configured to analyze the output of the detector 52 during or after the combined detection operation is complete to identify the corresponding material that is characterized by the resulting radiation at each position, and an indication of the material can also be included in each data point. Thus, each data point can provide an indication of a material deposit 16 existence for a corresponding position along the length of the passage 14. If mercury or another material of interest is found at a predetermined threshold (i.e., number or percent) of the portions of the inner surface 12, the detection unit 20 can further indicate to an operator that a cleaning or decontamination operation is required. In other cases, the analysis of the information collected by the detection device 10 can be performed outside of the device 10, e.g., in a computer that receives the data points from the detection device 10.

The data points can be stored and/or communicated from the detection unit 20. For example, in some cases, the detection device 10 can include a memory 58, such as a flash memory, in communication with the detection unit 20, and the memory 58 can be adapted to receive the information representative of the data points, store the information, and subsequently output the information. The data points can be retrieved from the memory 58 after the detection device 10 is removed from the passage 14 at the end of a combined operation for detecting materials along the passage 14. In addition or alternative, the data points can be communicated from the detection unit 20 while the detection device 10 is still in the passage 14, with or without storing the data points in a memory 58, e.g., before the detection device 10 has collected the information for all of the data points. In this regard, the detection device 10 can be configured to communicate the data points via a wired or wireless connection. For example, the electrical wire 32 of line 22 can provide an electrical communication connection between the detection device 10 and a receiver 60 that can be located outside of the passage 14. In addition, or alternative, the detection device 10 can include a wireless transmitter 62 that is configured to communicate wirelessly to the receiver 60 outside of the passage 14.

In some embodiments of the present invention, the detection device 10 can be configured to move itself through the passage 14, i.e., without requiring the device 10 to be pulled by the line 22. For example, as illustrated in FIG. 4, the detection device 10 can include a drive device 64 that is configured to rotate one or more of the wheels 42 to thereby advance the detection unit 20 through the passage 14. The drive device 64 can include one or more motors 66, each motor 66 engaged to one or more of the wheels 42 by a drive shaft, chain, belt, gear, or other connection. The drive device 64 can be controlled by the controller 54, which can be programmed to move the detection device 10 through the passage 14 at a particular speed, along a particular route, to particular positions in the passage 14, and/or according to a predetermined list of program instructions or commands. In some cases, the drive device 64 can be controlled by a remote controller 68, which can be located outside of the passage 14. For example, the receiver 60 can include the remote controller 68, and the remote controller 68 can communicate with the drive device 64 wirelessly or via the line 22. The line 22 is shown in FIG. 4 but can be omitted, e.g., if the drive device 64 is used to transport the detection device 10 and the detection unit 20 is configured to either transmit information wirelessly to the receiver 60 or store information until the drive device 64 is removed from the passage 14 at the end of a combined detection operation.

Power for operating the detection device 10 can be optionally provided by an internal power source 70, such as a battery, or via the line 22. For example, the battery 70 can provide electricity for operating the detection unit 20 and electrical, pneumatic, or hydraulic energy for otherwise operating the drive device 64. If a line 22 is provided to extend to the detection device 10, the line 22 can provide electrical, pneumatic, and/or hydraulic energy.

Figure 5:
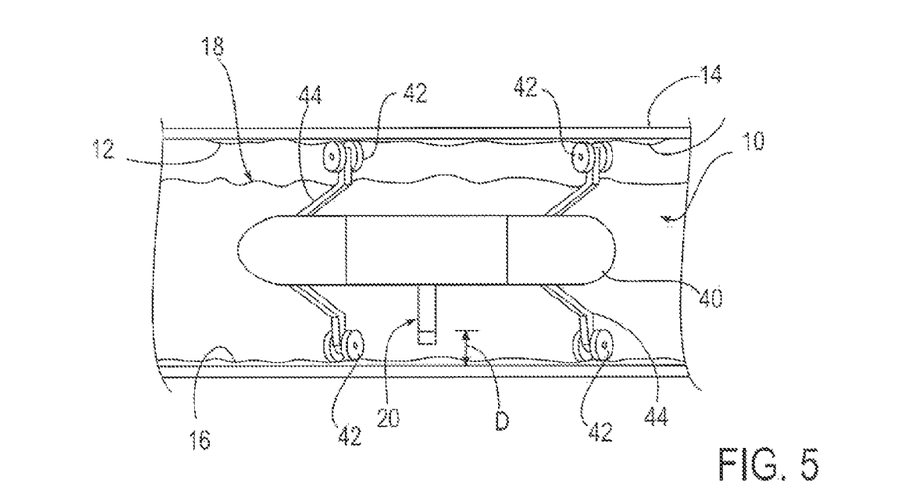
FIG. 5 is an elevation view illustrating a device according to another embodiment of the present invention, in which the device is configured to rotate in the passage.

The detection device 10 can be configured to inspect any portion of the inner surface 12 of the passage 14. In this regard, the detection unit 20 can operate at any or all times while the detection device 10 is transported along the length of the passage 14. Further, in some cases, the detection unit 20 can be configured to inspect different radial portions of the passage 14. For example, as shown in FIG. 5, each of the wheels 42 is configured to rotate about an axis that is disposed at an angle relative to both the longitudinal axis of the passage 14 and a plane perpendicular to the longitudinal axis. In this way, the detection unit 20 can be configured to rotate about an axis defined by the longitudinal axis of the passage 14 as the detection device 10 is transported through the passage 14. As described above, the detection device 10 can be transported either by power delivered to the wheels 42 or a force applied via a line 22 connected to the device 10. In either case, as the detection unit 20 moves through the passage 14 (longitudinally) and rotates about the longitudinal axis of the passage 14 (radially), the detection unit 20 is directed toward different portions of the inner surface 12 that generally define a helical path along the inner surface 12. The pitch of the helical path along the inner surface 12 is determined by the ratio of the longitudinal and radial motions of the detection device 10 through the passage 14. The pitch can be increased or decreased (e.g., to decrease or increase the number of data points taken along the length of the passage 14) by decreasing or increasing the number of turns that the detection device 10 makes for a particular longitudinal movement along the length of the passage 14.

The detector 52 can be positioned radially outward from the longitudinal axis of the detection device 10, and the detection device 10 can be configured so that the detector 52 is positioned radially outward from the longitudinal axis of the passage 14 when the detection device 10 is positioned in the passage 14. As shown in FIG. 5, the detection unit 20 can be configured to be positioned proximate the inner surface 12 of the passage 14, e.g., within a predetermined distance D of about 4 inches of the inner surface 12, such as within about 1 or 2 inches of the inner surface 12. With the detection unit 20 positioned proximate the inner surface 12, the energy required for providing the radiation can be reduced and the level of emissions received from the inner surface 12 can be increased. In some cases, e.g., with the detection unit 20 positioned proximate the inner surface 12, the detection device 10 can be adapted to operate even if the space between the detection unit 20 and the inner surface 12 is filled with liquid. In other words, the radiation can be emitted to the inner surface 12 of the passage 14 through a liquid, such as liquid hydrocarbon, and the resulting x-ray emission from the inner surface 12 can be detected through the liquid hydrocarbon. Thus, as shown in FIG. 5, the detection device 10 can be operated even while the passage 14 is full, or partially full, with liquid 18 such as crude oil or other hydrocarbon fluids. Further, as indicated by dashed lines in FIG. 5, the extension of the detection unit 20 from the housing 40 of the detection device 10 can be adjustable so that the detector 52 and/or the source 50 can be positioned closer or further from the inner surface 12 to optimize the detection operation. If the detection device 10 is operated while a fluid is flowing through the passage 14, the motion of the fluid can be used to transport the detection device 10 through the passage 14.

Figure 6:
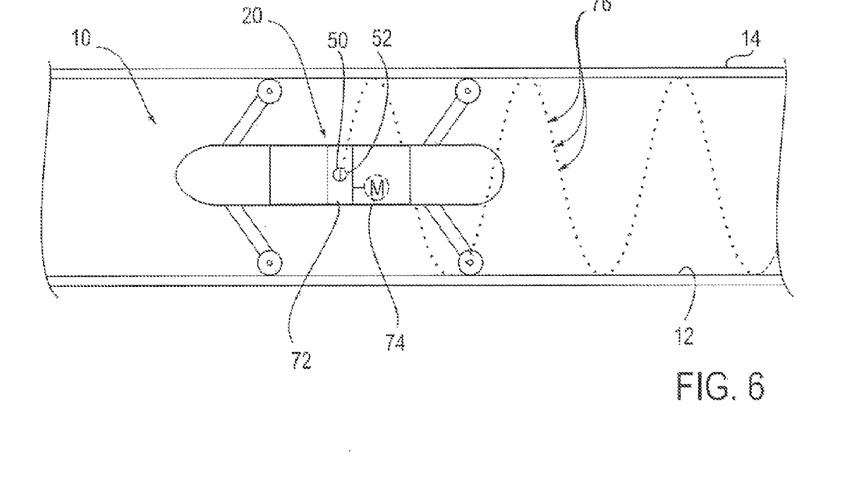
FIG. 6 is an elevation view illustrating a device according to another embodiment of the present invention, in which a detection head of the device is configured to rotate.
Figure 7:
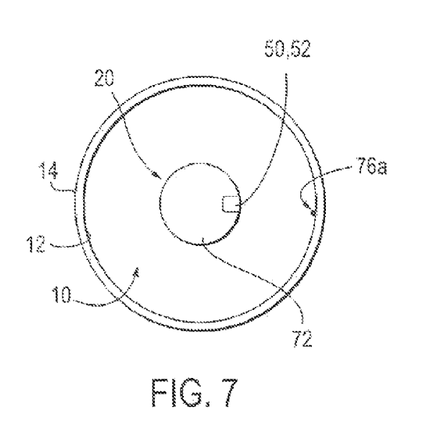
FIGS. 7 and 8 are elevation views illustrating the device of FIG. 6, as seen along the longitudinal axis of the passage.
Figure 8:
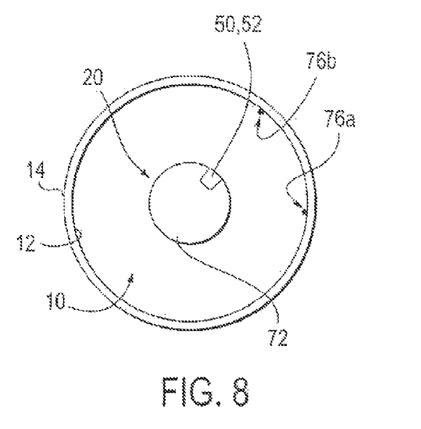

The detection unit 20 can be fixedly mounted on the detection device 10, as shown in FIG. 5, so that the configuration of the detection device 10 in the passage 14 also determines the position and orientation of the detection unit 20 and, hence, the portion of the inner surface 12 that can be identified by the detection unit 20. Alternatively, at least a portion of the detection unit 20 can be adjustably mounted on the device 10 so that the position and/or orientation of the detection unit 20 can be adjusted independently of the detection device 10. In particular, as shown in FIG. 6, the detection unit 20 can include a rotatable detection head 72, on which the detector 52 and/or the radiation source 50 are mounted so that the detector 52 and/or the source 50 can be selectively rotated. In this embodiment, the head 72 is rotatable about an axis that is generally parallel to the length of the passage 14 and the motion of the detection device 10 therethrough. The rotation of the head 72 is further illustrated in FIGS. 7 and 8. As shown in FIG. 7, the head 72 is directed toward a first portion 76a of the inner surface 12 of the passage 14 so that the detection unit 20 can identify the material at the first portion 76a of the inner surface 12. A motor or other actuation device 74 rotates the head 72 radially to a second position shown in FIG. 8 so that the detection unit 20 can identify the material at a second portion 76b of the inner surface 12. In this way, the head 72 can detect emissions from a plurality of portions (i.e., points or regions), which are collectively referred to by reference numeral 76, and which define an arc on the inner surface 12 of the passage 14.

The head 72 can rotate while the detection device 10 is otherwise stationary in the passage 14, so that the detection device 10 can identify materials at two positions or portions 76 that are radially different but located at a similar longitudinal position of the passage 14. Alternatively, the head 72 can rotate the detection unit 20 while the detection device 10 is transported through the passage 14 so that the detection unit 20 identifies the material of the inner surface 12 at a series of portions 76 that generally define a helical path in the passage 14, as illustrated in FIG. 6. In either case, the actuation device 74 can be controlled in a manner similar to the motion of the detection device 10, e.g., by the controller 54, by an operator or automatic program that controls the operation via the remote controller 68, or the like.

Figure 9:
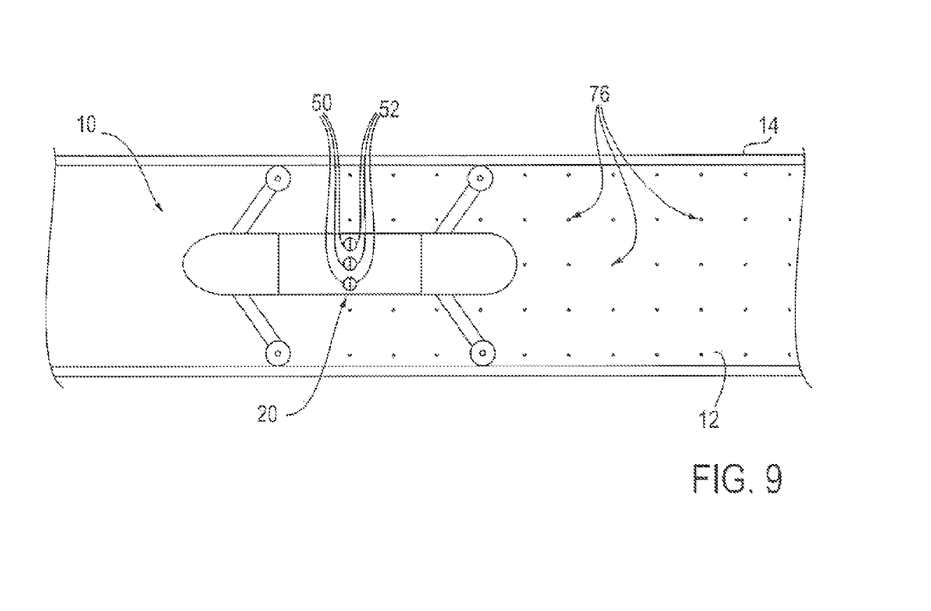
FIG. 9 is an elevation view illustrating a device according to another embodiment of the present invention, in which the detection unit includes a plurality of detectors.
Figure 10:
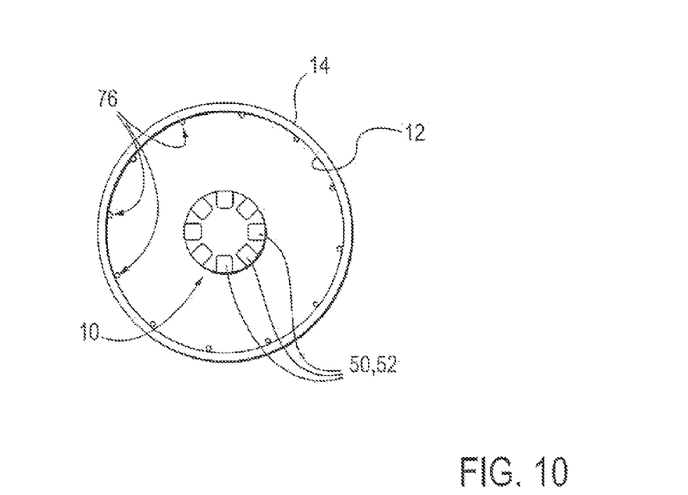
FIG. 10 is an elevation view illustrating the device of FIG. 9, as seen along the longitudinal axis of the passage.

In some cases, the detection unit 20 can include a plurality of detectors 52 and/or radiation sources 50 so that the unit 20 can detect emissions from a plurality of portions on the inner surface 12 even if the detection unit 20 remains stationary. In this regard, FIGS. 9 and 10 illustrate an embodiment in which the detection unit 20 includes eight detectors 52 that are disposed at successive radial positions so that the detectors 52 can simultaneously detect emissions from a plurality of portions that define an arc on the inner surface 12 of the passage 14. In the illustrated embodiment, eight sources 50 are also provided, each source 50 corresponding to one of the detectors 52; however, in other embodiments, each source 50 can be configured to provide radiation to two or more of the portions 76 from which the emissions are detected. Thus, the number of sources 50 can be lesser than the number of detectors 52, e.g., with one, two, or four sources 50 provided for eight detectors 52.

As shown in FIGS. 9 and 10, the detectors 52 can identify the material of the inner surface 12 at a plurality of portions 76 that are spaced radially and/or longitudinally. Thus, even if the detection device 10 does not rotate in the passage 14, the device 10 can nevertheless determine the material at positions around the inner circumference of the passage 14. It is appreciated that the number of detectors 52 and the frequency of the individual detection operations can be adjusted according to the desired resolution of the data points. In some cases, the data points can correspond to portions 76 of the inner surface 12 that are no more than an inch (or no more than a fraction of an inch) from one another.

The detection device 10 can be used to check for mercury or other material deposits 16 in the passage 14 at regular intervals, during other maintenance operations, or before and/or after cleaning operations to determine the effectiveness of the cleaning operations. Further, the methods for detecting mercury or other materials can be performed in combination with other operations. For example, the detection device 10 can be integrally formed with a conventional pipeline pig or other machine that is transported through the passage 14 for cleaning of the passage 14, and the detection device 10 can be used to detect mercury or other particular materials before, after, and/or during a cleaning operation performed with the pig.

The detection device 10 can be used to detect deposits 16 of various types of materials, e.g., other than or in addition to mercury, in the passage 14. In this regard, the detection unit 20 can be programmed to identify any number of different materials according to the XRF emission emitted therefrom. In some cases, the detection unit 20 can determine, or provide information for determining, the exact and complete content of the material at the inner surface 12 of the passage 14, e.g., by identifying a plurality of elemental materials and the percent of each material identified at the inner surface 12. Further, the detection device 10 can include a camera or other equipment for providing visual imagery of the inside of the passage 14.

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method for detecting material deposits on an inner surface of a pipe for transporting hydrocarbon fluids, the method comprising:

transporting a detection device through the pipe, the detection device including an x-ray fluorescence detection unit;

operating the x-ray fluorescence detection unit such that the detection unit in the pipe emits a radiation emission toward the inner surface of the pipe to excite a portion of the inner surface and detects a resulting x-ray emission from the portion of the inner surface to identify a material deposit on the inner surface of the pipe; and repeating the operating step with the detection unit at successive positions along a length of the pipe to thereby generate a plurality of data points, each data point providing an indication of a material deposit existence for a corresponding position along the length of the pipe.

2. A method according to claim 1 wherein operating the x-ray fluorescence detection unit comprises identifying a mercury deposit on the inner surface of the pipe.

3. A method according to claim 1, further comprising providing a line connected to the detection device and wherein said transporting step comprises pulling the detection device through the passage via the line extending through the pipe.

4. A method according to claim 1, further comprising storing information representative of the data points in a memory of the detection device and subsequently outputting the information from the detection device.

5. A method according to claim 1, further comprising communicating information representative of the data points from the detection device while the detection device is disposed in the pipe.

6. A method according to claim 5, wherein communicating the information comprises communicating the information wirelessly to a receiver disposed outside of the pipe.

7. A method according to claim 5, wherein communicating the information comprises communicating the information via a wire extending from the detection device to a receiver disposed outside of the pipe.

8. A method according to claim 1, wherein said operating step comprises rotating a detection head of the detection unit to thereby detect emissions from a plurality of portions defining an arc on the inner surface of the pipe.

9. A method according to claim 1, wherein said operating step comprises operating a plurality of detectors of the x-ray fluorescence detection unit to thereby detect emissions from a plurality of portions defining an arc on the inner surface of the pipe.

10. A method according to claim 1, wherein said operating step comprises positioning the detection unit within 1 inch of the inner surface of the pipe.

11. A method according to claim 1, further comprising identifying a plurality of materials at the inner surface of the pipe.

12. A method for detecting material deposits on an inner surface of an enclosed passage, the method comprising:
    providing a plurality of wheels for supporting a detection unit in the passage, the detection device including an x-ray fluorescence detection unit;
    driving at least one of the wheels to thereby transport the detection device through the passage;
    operating the x-ray fluorescence detection unit such that the detection unit in the passage emits a radiation emission toward the inner surface of the passage to excite a portion of the inner surface and detects a resulting x-ray emission from the portion of the inner surface to identify a material deposit on the inner surface; and
    repeating the operating step with the detection unit at successive positions along a length of the passage to thereby generate a plurality of data points, each data point providing an indication of a material deposit existence for a corresponding position along the length of the passage.

13. A method according to claim 12 wherein operating the x-ray fluorescence detection unit comprises identifying a mercury deposit on the inner surface of the passage.

14. A method according to claim 12 wherein said operating step comprises rotating a detection head of the detection unit to thereby detect emissions from a plurality of portions defining an arc on the inner surface of the passage.

15. A method according to claim 12 wherein said operating step comprises operating a plurality of detectors of the x-ray fluorescence detection unit to thereby detect emissions from a plurality of portions defining an arc on the inner surface of the passage.

16. A method according to claim 12 wherein said operating step comprises positioning the detection unit within 1 inch of the inner surface of the passage.

17. A method according to claim 12, further comprising identifying a plurality of materials at the inner surface of the passage.

18. A method for detecting material deposits on an inner surface of a pipe for transporting liquid hydrocarbon fluids, the method comprising:
    transporting a detection device through the pipe while the pipe is at least partially full of liquid hydrocarbon, the detection device including an x-ray fluorescence detection unit;
    operating the x-ray fluorescence detection unit such that the detection unit in the pipe emits a radiation emission through the liquid hydrocarbon to the inner surface of the pipe to excite a portion of the inner surface and detects a resulting x-ray emission from the portion of the inner surface through the liquid hydrocarbon to identify a material deposit on the inner surface of the pipe; and
    repeating the operating step with the detection unit at successive positions along a length of the pipe to thereby generate a plurality of data points, each data point providing an indication of a material deposit existence for a corresponding position along the length of the pipe.

19. A method according to claim 18, wherein operating the x-ray fluorescence detection unit comprises identifying a mercury deposit on the inner surface of the pipe.

20. A method according to claim 18, wherein said operating step comprises rotating a detection head of the detection unit to thereby detect emissions from a plurality of portions defining an arc on the inner surface of the pipe.

21. A method according to claim 18, wherein said operating step comprises operating a plurality of detectors of the x-ray fluorescence detection unit to thereby detect emissions from a plurality of portions defining an arc on the inner surface of the pipe.

22. A method according to claim 18, wherein said operating step comprises positioning the detection unit within 1 inch of the inner surface of the pipe.

23. A method according to claim 18, further comprising identifying a plurality of materials at the inner surface of the pipe.

* * * * *